(12) United States Patent
Korvick et al.

(10) Patent No.: US 8,029,520 B2
(45) Date of Patent: Oct. 4, 2011

(54) METHOD FOR PERFORMING TRANS-ANAL RESECTION WITH A CURVED CUTTER STAPLER

(75) Inventors: Donna L. Korvick, Maineville, OH (US); William A. Bernie, Naples, FL (US); Antonio Longo, Palermo (IT)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1398 days.

(21) Appl. No.: 11/348,544

(22) Filed: Feb. 7, 2006

(65) Prior Publication Data
US 2007/0185508 A1 Aug. 9, 2007

(51) Int. Cl.
*A61B 17/08* (2006.01)

(52) U.S. Cl. ...... 606/153; 606/144; 606/151; 227/180.1

(58) Field of Classification Search .......... 606/144–148, 606/153–157, 219, 139; 227/180.1, 19
See application file for complete search history.

(56) References Cited

U.S. PATENT DOCUMENTS

| | | | | |
|---|---|---|---|---|
| 4,207,898 A * | 6/1980 | Becht | ......................... | 227/179.1 |
| 4,606,343 A * | 8/1986 | Conta et al. | ................. | 227/178.1 |
| 5,360,154 A * | 11/1994 | Green | ......................... | 227/179.1 |
| 5,441,507 A * | 8/1995 | Wilk | ............................. | 606/139 |
| 5,679,658 A * | 10/1997 | Elson | ............................. | 514/55 |
| 6,050,472 A * | 4/2000 | Shibata | ....................... | 227/175.2 |
| 6,083,241 A * | 7/2000 | Longo et al. | ................... | 606/219 |
| 6,102,271 A * | 8/2000 | Longo et al. | ................ | 227/180.1 |
| 6,302,311 B1 * | 10/2001 | Adams et al. | ............... | 227/176.1 |
| 6,629,630 B2 * | 10/2003 | Adams | ........................ | 227/180.1 |
| 6,688,312 B2 * | 2/2004 | Yeretsian | ....................... | 128/898 |
| 6,805,273 B2 * | 10/2004 | Bilotti et al. | ................ | 227/180.1 |
| 6,955,643 B2 * | 10/2005 | Gellman et al. | .............. | 600/104 |
| 6,959,851 B2 * | 11/2005 | Heinrich | ..................... | 227/175.1 |
| 7,318,830 B2 * | 1/2008 | Mayoral | ........................ | 606/139 |
| 2003/0183671 A1 * | 10/2003 | Mooradian et al. | ......... | 227/175.1 |
| 2003/0233108 A1 * | 12/2003 | Gellman et al. | .............. | 606/144 |
| 2004/0084505 A1 * | 5/2004 | Bilotti et al. | ................ | 227/180.1 |
| 2004/0217146 A1 * | 11/2004 | Beck | ........................... | 227/176.1 |
| 2004/0222268 A1 * | 11/2004 | Bilotti et al. | ................ | 227/180.1 |
| 2004/0254590 A1 * | 12/2004 | Hoffman et al. | ............... | 606/139 |
| 2005/0228414 A1 * | 10/2005 | Mayoral | ........................ | 606/153 |
| 2005/0228446 A1 * | 10/2005 | Mooradian et al. | ........... | 606/215 |
| 2006/0049231 A1 * | 3/2006 | Leiboff et al. | .............. | 227/180.1 |
| 2006/0144897 A1 * | 7/2006 | Jankowski et al. | ......... | 227/175.1 |
| 2006/0167473 A1 * | 7/2006 | Scheyer | ......................... | 606/139 |
| 2007/0181631 A1 * | 8/2007 | Bilotti et al. | ............... | 227/179.1 |

* cited by examiner

*Primary Examiner* — Darwin Erezo
*Assistant Examiner* — Mark Mashack
(74) *Attorney, Agent, or Firm* — Welsh Flaxman & Gitler LLC (57) ABSTRACT

A method for performing trans-anal resection is achieved by applying a first stitch about the rectum, wherein deep bites of the first stitch capture and fold a rectum wall, creating a longitudinal staple line in the rectal wall at a position adjacent the first stitch, positioning a curved surgical stapler instrument in the rectum for capturing the rectal wall held by the first stitch, firing the surgical stapler instrument creating a circumferential first staple line approximately along the arc defined by the first stitch, and repeating the procedure about the circumference of the rectum until a predetermined portion of the rectum is fully resected.

10 Claims, 12 Drawing Sheets

METHOD FOR PERFORMING TRANS-ANAL RESECTION WITH A CURVED CUTTER STAPLER

BACKGROUND OF THE INVENTION

1. Field of the Invention

The present invention relates to a surgical stapling and cutting instrument adapted for use in trans-anal resection and an associated method for performing trans-anal resection. More particularly, the present invention relates to a surgical stapling and cutting instrument having a curvature particularly adapted to fit within the rectum adjacent the anal canal for the performance of the trans-anal resection as well as the method for using the surgical stapling and cutting instrument.

2. Description of the Prior Art

Surgical stapling and cutting instruments are commonly utilized in the diagnosis and treatment of pathologies treated by staple resection. Surgical stapling instruments provide a mechanism to extend the transluminal exploitation of mechanical suturing devices introduced via the anal canal, mouth, stomach and service accesses. Although surgical stapling and cutting instruments are most commonly utilized with rectal pathologies, surgical stapling and cutting instruments may be used in a variety of environments.

Surgical stapling and cutting instruments generally include a support frame, an anvil attached to the support frame and a cartridge module carrying a plurality of staples. The instruments also include a driver within the cartridge module which pushes all of the staples out simultaneously into the anvil to form the staples into a generally B-shape, suturing tissue together. In addition, these instruments include approximation mechanisms for moving the cartridge module from a spaced position relative to the anvil to accept tissue therebetween to a closed position where the tissue is clamped between the anvil and the cartridge module. Finally, the instruments include a firing means for moving the staple driver forward to form the staples against the anvil.

In addition to other procedures, surgical stapling and cutting instruments have been utilized in conjunction with trans-anal resections. Trans-anal resection is a surgical procedure utilized to remove tissue, for example, tumorous tissue, within the rectum by operating through the anus. This procedure is commonly performed to treat early stage rectal cancer or rectal tumors close to the anus. In accordance with this procedure, a section of the rectum is removed and the remaining opposed edges are coupled to complete the linking of the anus with the remainder of the rectum.

With the foregoing in mind, those skilled in the art will appreciate the need for more advanced procedures relating to trans-anal resection, as well as the need for advanced instruments specifically designed to facilitate the advanced surgical procedures. The present invention addresses this need through the provision of a technique for trans-anal resection and an associated curved cutter stapler adapted for assisting in the performance of the procedure.

SUMMARY OF THE INVENTION

It is, therefore, an object of the present invention to provide a method for performing trans-anal resection. The method is achieved by applying a first stitch about the rectum, wherein deep bites of the first stitch capture and fold a rectum wall, creating a longitudinal staple line in the rectal wall at a position adjacent the first stitch, positioning a curved surgical stapler instrument in the rectum for capturing the rectal wall held by the first stitch, firing the surgical stapler instrument creating a circumferential first staple line approximately along the arc defined by the first stitch, and repeating the procedure about the circumference of the rectum until a predetermined portion of the rectum is fully resected.

It is also an object of the present invention to provide a method wherein the first stitch is a whip stitch.

It is another object of the present invention to provide a method wherein the first stitch is applied from a one o'clock position to a ten o'clock position.

It is a further object of the present invention to provide a method wherein the first stitch is complemented by the application of a traction suture positioned beneath the first stitch to maintain tension on the tissue as the procedure is performed.

It is also another object of the present invention to provide a method wherein the longitudinal staple line is applied between the first stitch and the traction suture.

It is still another object of the present invention to provide a method including the step of applying a suture at the meeting point of adjacent staple lines.

It is yet a further object of the present invention to provide a method wherein the suture is a figure eight suture.

It is also an object of the present invention to provide a method wherein the surgical stapler instrument includes a frame having a proximal end and a distal end, with a handle positioned at the proximal end and an end effector positioned at the distal end. The end effector is shaped and dimensioned for supporting a cartridge module. A firing mechanism is associated with the end effector and the cartridge module for selective actuation. The end effector has a radius of curvature optimized for trans-anal resection such that the end effector has a curvature of at most about 40 mm diameter.

It is another object of the present invention to provide a method wherein the end effector has a curvature of between approximately a 20 mm diameter and approximately a 40 mm diameter.

It is a further object of the present invention to provide a method wherein the end effector has curvature adapted to fit within an envelope having a diameter of approximately 40 mm.

Other objects and advantages of the present invention will become apparent from the following detailed description when viewed in conjunction with the accompanying drawings, which set forth certain embodiments of the invention.

DESCRIPTION OF THE PREFERRED EMBODIMENTS

The detailed embodiments of the present invention are disclosed herein. It should be understood, however, that the disclosed embodiments are merely exemplary of the invention, which may be embodied in various forms. Therefore, the details disclosed herein are not to be interpreted as limiting, but merely as the basis for teaching one skilled in the art how to make and/or use the invention.

Figure 1:
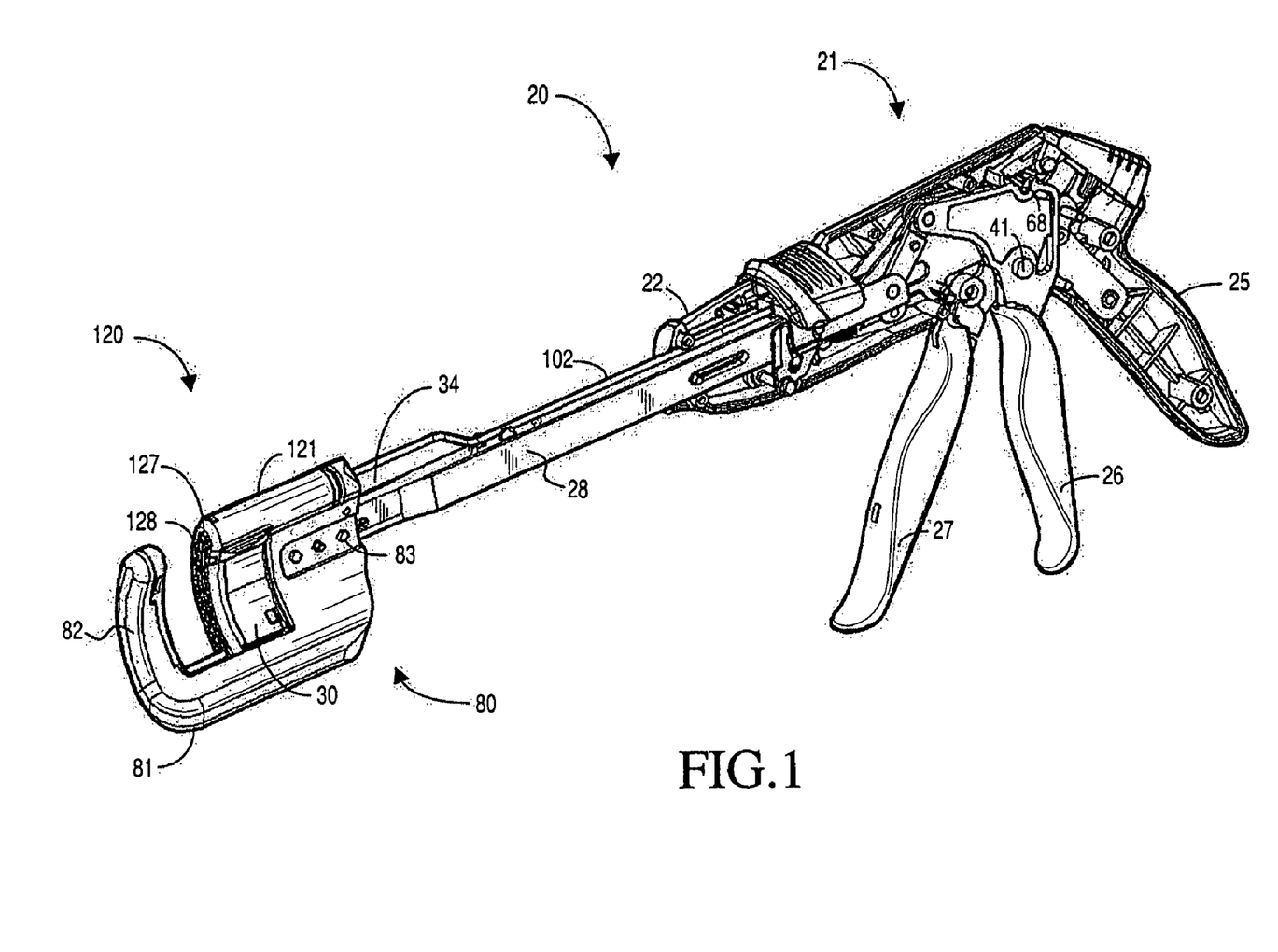
FIG. 1 is a perspective view of the surgical stapler in accordance with the present invention.

Referring to FIG. 1 in combination with FIGS. 2 to 5, there is shown a surgical stapling and cutting instrument, in particular, a linear surgical stapler 20 which is designed to staple and cut tissue. The linear surgical stapler 20 has a handle 21 at a first proximal end and an end effector 80 at an opposite distal end. The end effector 80 is curved in accordance with a preferred embodiment of the present invention. Right and left hand structural plates (often called "handle plates") 34, 35, respectively, connect the handle 21 to the end effector 80 of the instrument (the left hand handle plate 35 is removed and not shown in FIG. 1). The handle 21 has a right hand shroud 22 coupled to a left hand shroud (the left hand shroud is not shown in FIG. 1). The handle 21 also has a body portion 23 to grip and maneuver the linear surgical stapler 20 (see FIGS. 2 to 5).

The linear surgical stapler 20 in accordance with the present invention is particularly adapted for use in the performance of trans-anal resection. In particular, access to, and the performance of procedures adjacent to, the anus are made difficult by the limited size of the anus and rectum. The present surgical stapler 20 is specifically shaped and dimensioned for access through the anus and alignment within the rectum during trans-anal resection. In particular, the end effector 80 of the linear surgical stapler 20 is adapted to fit and function within a circular envelope having a diameter of at most 40 mm. With this in mind, and in accordance with a preferred embodiment of the present invention, the linear surgical stapler 20 has a distal end with a tissue end effector 80 having a curvature between a diameter of approximately 20 mm to approximately 40 mm, and more preferably, approximately 36 mm, in order to fit into a minimum oval envelope permitting passage through the anus and performance of a rectal resection procedure. In accordance with a preferred embodiment, an effector having a curvature with a diameter of approximately 36 mm would be structured such that it defines an arc length of approximately 30 mm.

Figure 6:
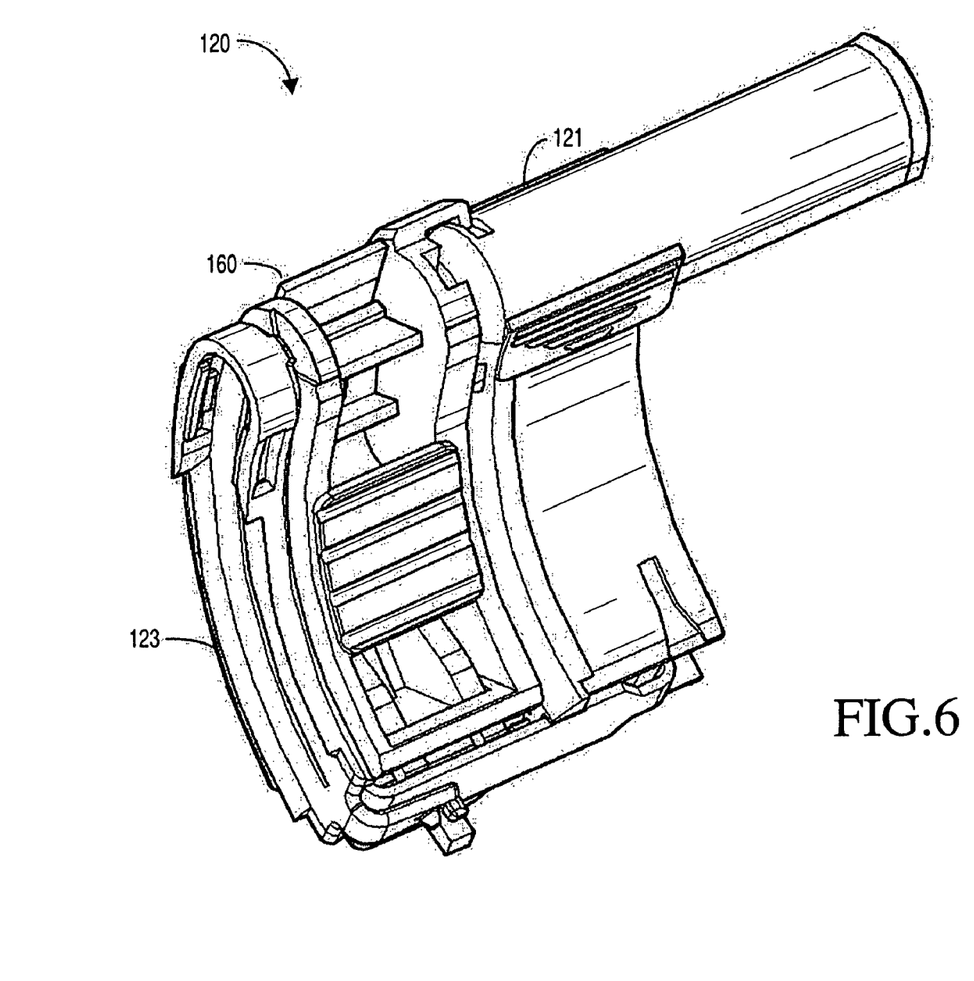
FIG. 6 is a front perspective view of the cartridge module with the retainer secured thereto.
Figure 7:
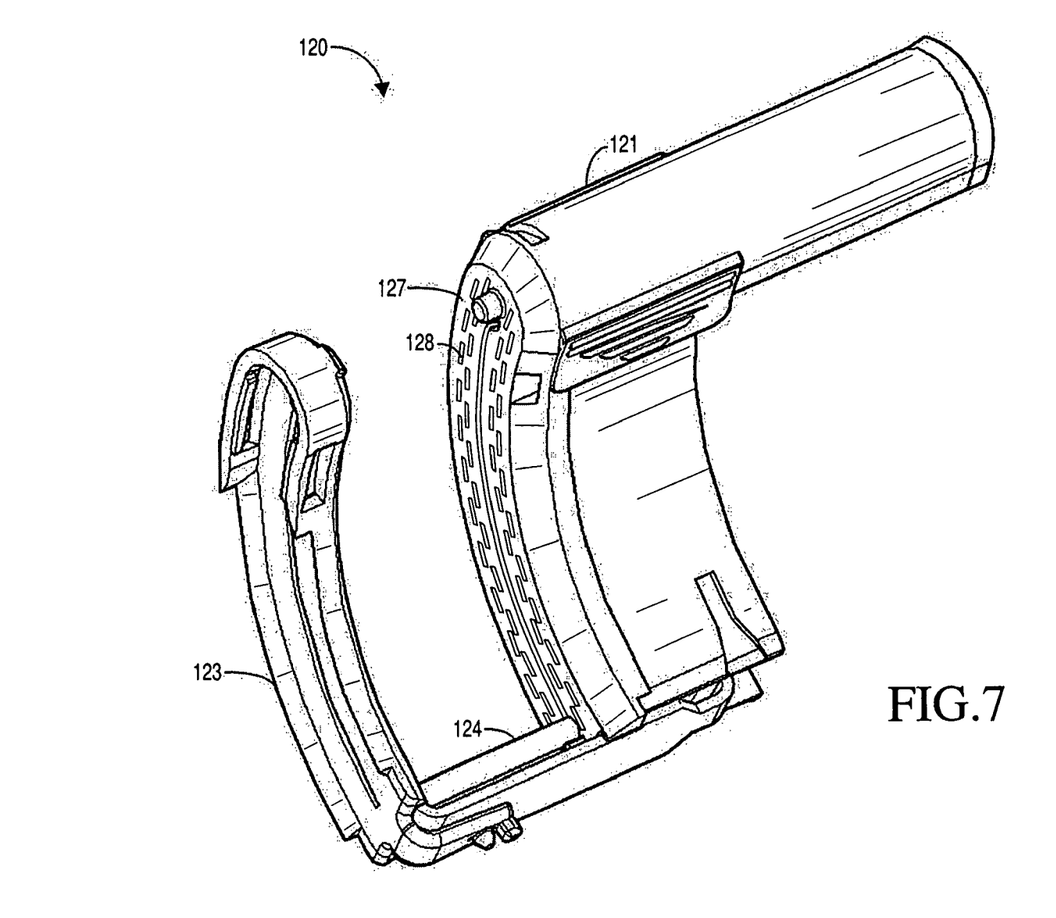
FIG. 7 is a front perspective view of the cartridge module with the retainer removed.

The end effector 80 is a surgical fastening assembly that includes a cartridge module 120 (see FIGS. 6 and 7) and a C-shaped supporting structure 81. The term C-shaped is used throughout the specification to describe the concave nature of the supporting structure 81 and the cartridge module 120. The C-shaped construction facilitates enhanced functionality and the use of the term "C-shaped" in the present specification should be construed to include a variety of concave shapes which would similarly enhance the functionality of surgical stapling and cutting instruments. The distal end 30 of a closure member 28 is disposed to receive the cartridge module 120. The end effector 80 also includes a safety lockout mechanism (not shown) for preventing the firing of a previously fired cartridge module 120. The cartridge module 120 contains a cartridge housing 121 coupled to an anvil 122. The cartridge module 120 also includes a retaining pin 125, a knife 126, a removable retainer 160, a tissue contacting surface 127 which displays a plurality of staple-containing slots 128 in staggered formation in one or more rows (that is, staple lines) on either side of the knife 126. Staples (not shown) are fired from the cartridge housing 121 against the staple-forming surface 129 of the anvil 122 that faces the tissue-contacting surface 127 of the cartridge housing 121.

As will become apparent based upon the following disclosure, the present linear surgical stapler 20 is designed as a multiple firing device with a replaceable cartridge module 120. However, it should be understood that many of the underlying concepts of the present invention may be equally applied in single firing devices without departing from the spirit of the present invention. While the present end effector 80 is disclosed below as being adapted for use in conjunction with a replaceable cartridge module 120 having various components, the concepts underlying the present invention could be applied to a variety of end effectors and cartridge module constructions without departing from the spirit of the present invention.

The supporting structure 81 of the end effector 80 is respectively attached to the right and left handle plates 34, 35, by a shoulder rivet 82 and posts 83 which extend from the supporting structure 81 into receiving holes in the handle plates 34, 35. In accordance with a preferred embodiment of the present invention, the supporting structure 81 is formed via a single piece construction. More specifically, the supporting structure 81 is formed by extrusion, for example, of aluminum, with subsequent machining to create the supporting structure 81 disclosed in accordance with the present invention. By constructing the supporting structure 81 in this manner, multiple parts are not required and the associated cost of manufacture and assembly is substantially reduced. In addition, it is believed the unitary structure of the supporting structure 81 enhances the overall stability of the present linear surgical stapler 20. In addition, the unitary extruded structure of the supporting structure 81 provides for a reduction in weight, easier sterilization since cobalt irradiation will effectively penetrate the extruded aluminum and less trauma to tissue based upon the smooth outer surface achieved via extrusion.

The handle 21 of the linear surgical stapler 20 includes a hand grip 24 which the surgeon grasps with the palm of his hand (see FIGS. 2 to 5). The hand grip 24 is composed of a right hand shroud handle 25 (see FIG. 1) and a left hand shroud handle (the left hand shroud handle is not shown in FIG. 1). Pivotally extending from the underside of the handle 21 are a closure trigger 26 and a firing trigger 27. The linear surgical stapler 20 illustrated in FIG. 1 is shown with the closure and firing triggers 26, 27 in their unactuated positions and with a cartridge module 120 inserted and the retainer 160 removed. Consequently, the cartridge housing 121 is spaced from the anvil 122 for the placement of tissue between the cartridge housing 121 and the anvil 122.

The handle 21 of the linear surgical stapler 20 contains a tissue retaining pin actuation mechanism 100. The tissue retaining pin actuation mechanism 100 includes a saddle shaped slide 101 positioned on the top surface of the handle 21. Manual movement of the slide 101 results in distal movement of the push rod 102. The push rod 102 is coupled to the retaining pin 125 of the cartridge module 120. The distal movement or proximal retraction of the push rod 102 results in corresponding movement of the retaining pin 125. The retaining pin actuation mechanism 100 is also releasably coupled to the closure trigger 26 within the handle 21 such that actuation of the closure trigger 26 will result in automatic distal movement of the retaining pin 125 if it has not already been manually moved to its most proximal position.

Figure 2:
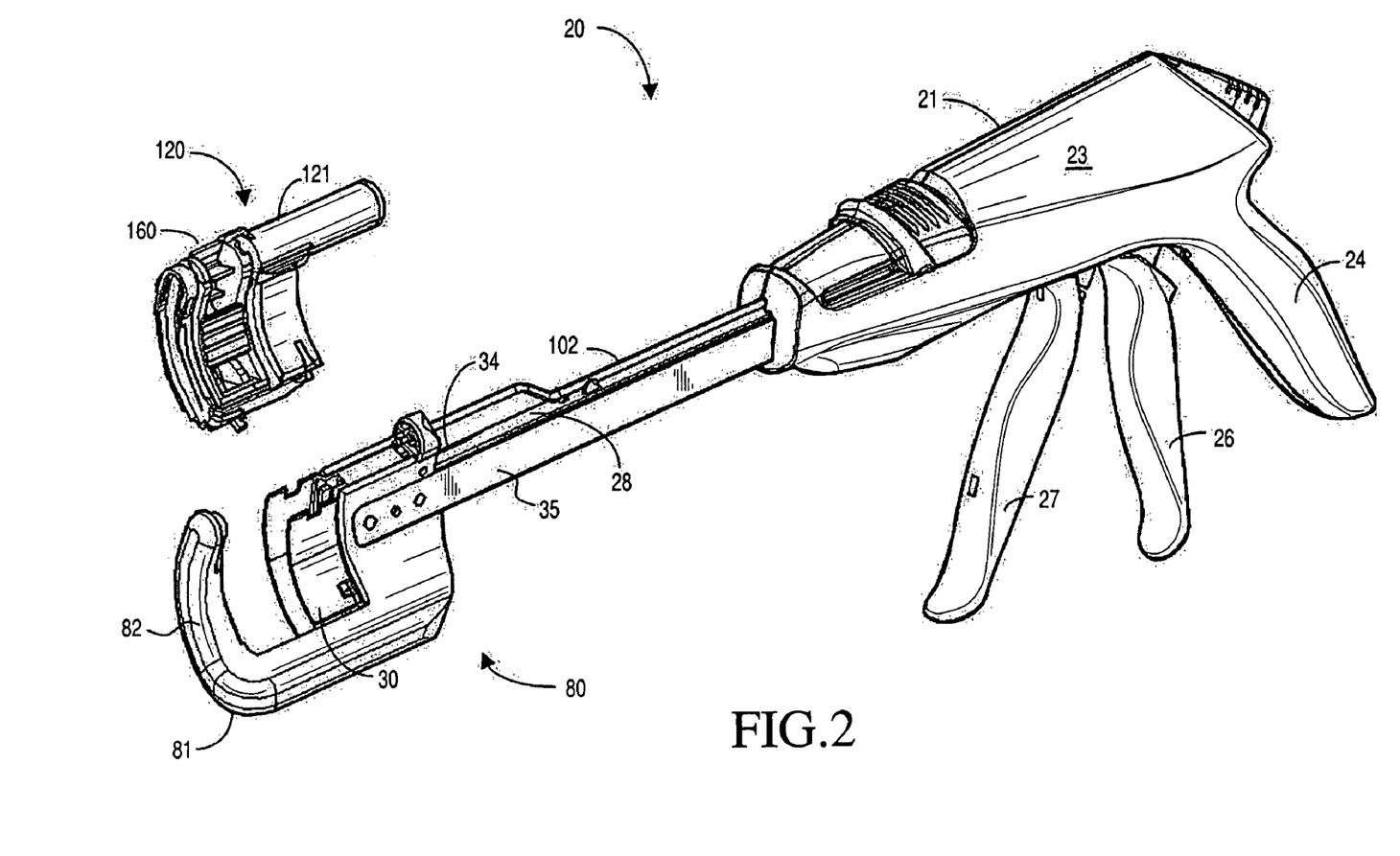
FIG. 2 is perspective view of the surgical stapler with the cartridge module removed.

Referring briefly to FIGS. 2 to 5, there is illustrated what happens when the cartridge module 120 is loaded and the closure and firing triggers 26, 27 are sequentially squeezed toward the hand grip 24 to actuate the end effector 80 of the linear surgical stapler 20. The linear surgical stapler 20 is loaded with the cartridge module 120, as shown in FIG. 2, and the retainer 160 is removed. The linear surgical stapler 20 is now ready to receive tissue as shown in FIG. 1.

Figure 3:
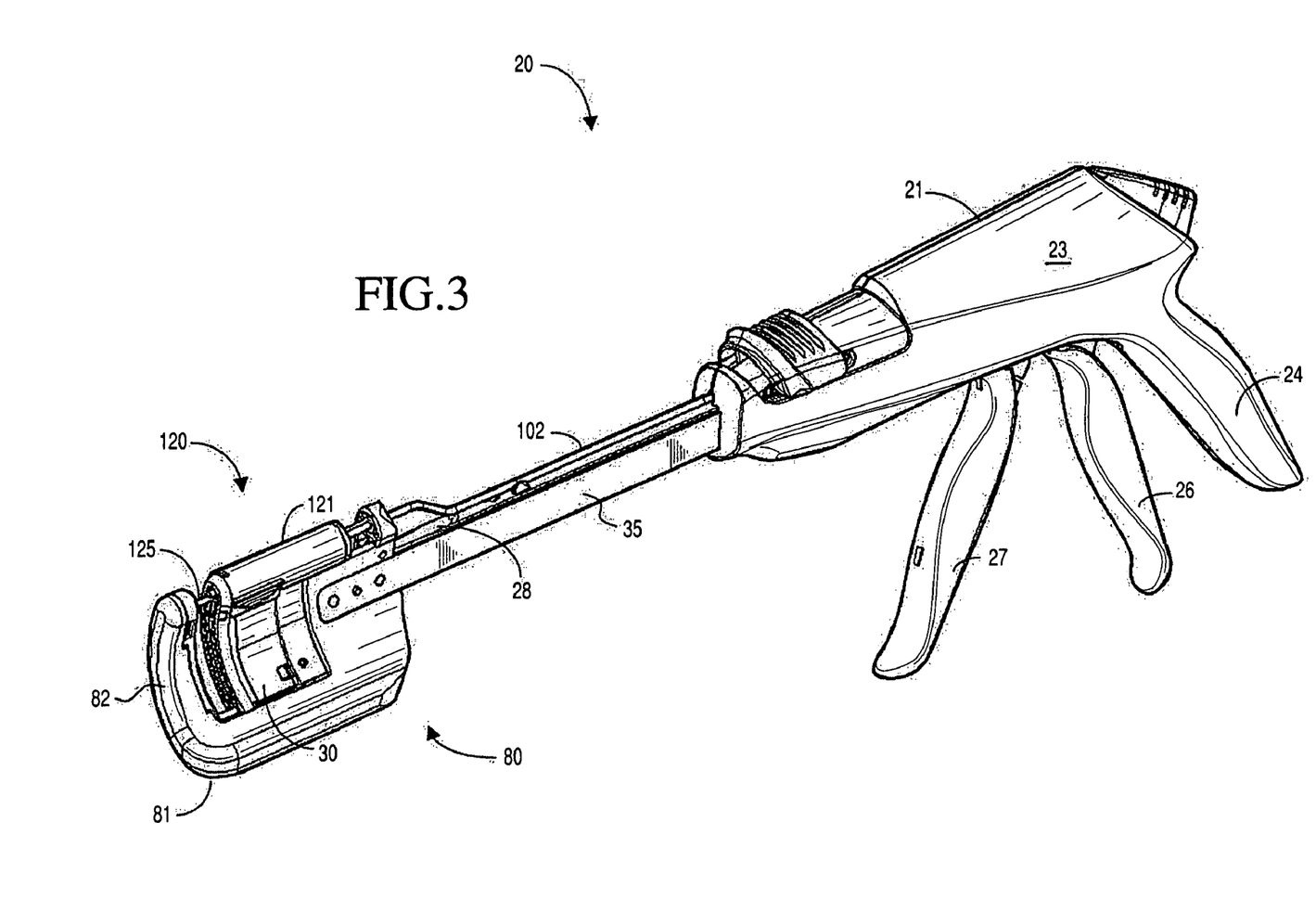
FIG. 3 is a perspective view of the surgical stapler with the cartridge housing moved to an intermediate position.

When the closure trigger 26 is partially squeezed to rest in its first detent position shown in FIG. 3, the cartridge housing 121 moves from its fully opened position to an intermediate position between the open and closed positions as discussed below in greater detail. Simultaneously, the tissue retaining pin actuation mechanism 100 moves the retaining pin 125 forward from the cartridge housing 121 through an opening in the anvil 122. In this position, tissue which has been placed between the cartridge housing 121 and the anvil 122 can be properly positioned, and the retention of the tissue between the cartridge housing 121 and the anvil 122 is assured. Therefore, when the closure trigger 26 has been actuated to its intermediate position, the cartridge housing 121 and anvil 122 are correspondingly positioned in their tissue retaining positions.

Figure 4:
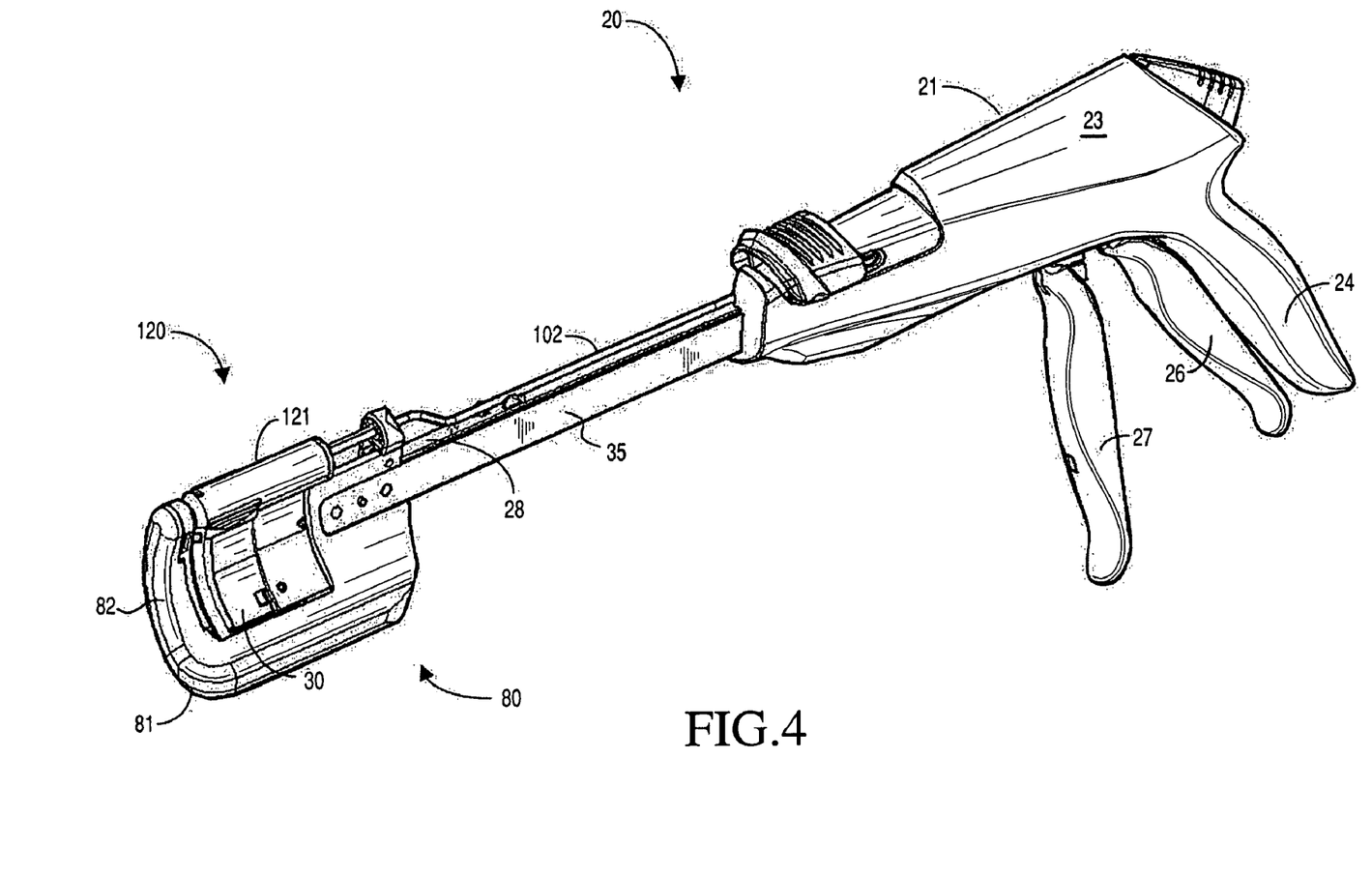
FIG. 4 is a perspective view of the surgical stapler with the cartridge housing moved to a closed position.
Figure 5:
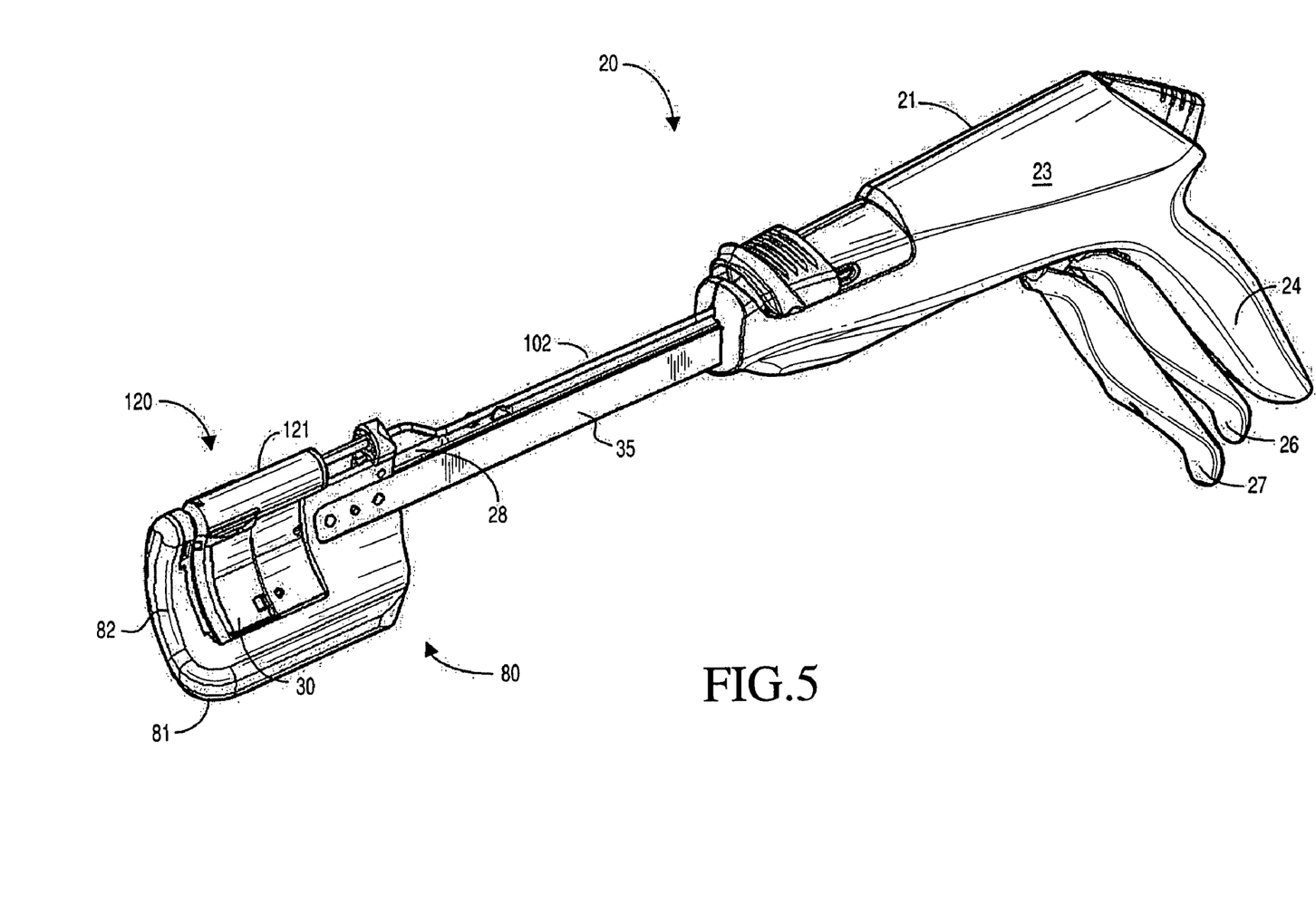
FIG. 5 is a perspective view of the surgical stapler with the firing trigger in a firing position.

When the closure trigger 26 is fully squeezed so that it is adjacent the forward end of the hand grip 24, as illustrated in FIG. 4, the tissue contacting surface 127 of the cartridge housing 121 and the staple-forming surface 129 of the anvil 122 are adjacent to each other, and the properly positioned and retained tissue is consequently fully clamped. Additionally, the firing trigger 27 has rotated counterclockwise toward the handgrip 24 to enable the surgeon to grasp the firing trigger 27 for the firing of staples. Accordingly, the firing trigger 27 is now in position for the surgeon to squeeze it to staple and cut the tissue. When the firing trigger 27 has been fully squeezed to fire the staples, as shown in FIG. 5, the firing trigger 27 rests in near proximity to the closure trigger 26.

The present linear surgical stapler is constructed in a manner similar to commonly owned and copending applications. As such, further details regarding the structure and operation of the linear surgical stapler 20 may be found in commonly owned U.S. patent application Ser. No. 11/014,910, filed Dec. 20, 2004, entitled "CURVED CUTTER STAPLER SHAPED FOR MALE PELVIS", which is incorporated herein by reference.

Figures 8, 9:
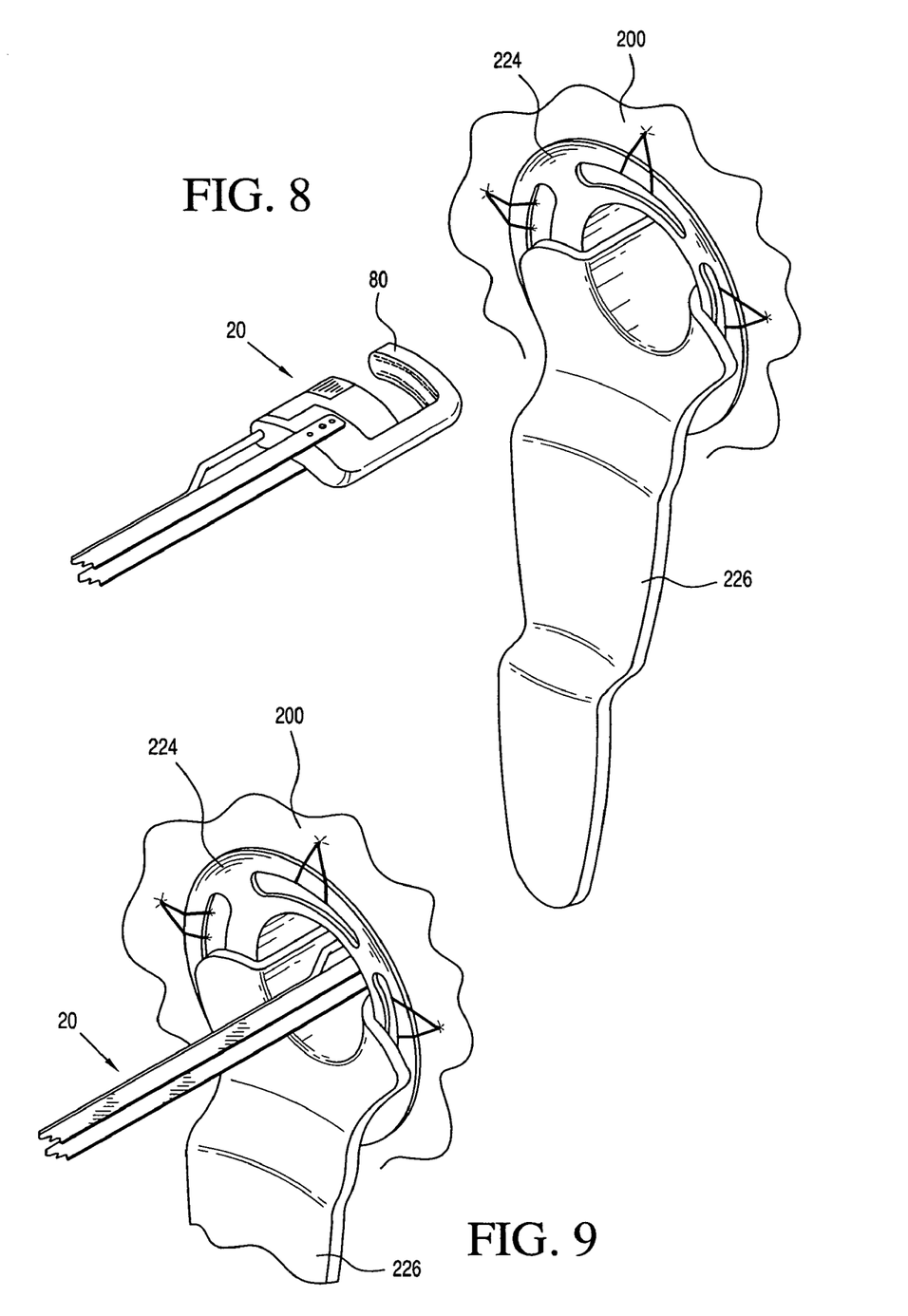
FIGS. 8 to 16 disclose the various steps in performing a trans-anal resection in accordance with the present invention.
Figure 10:
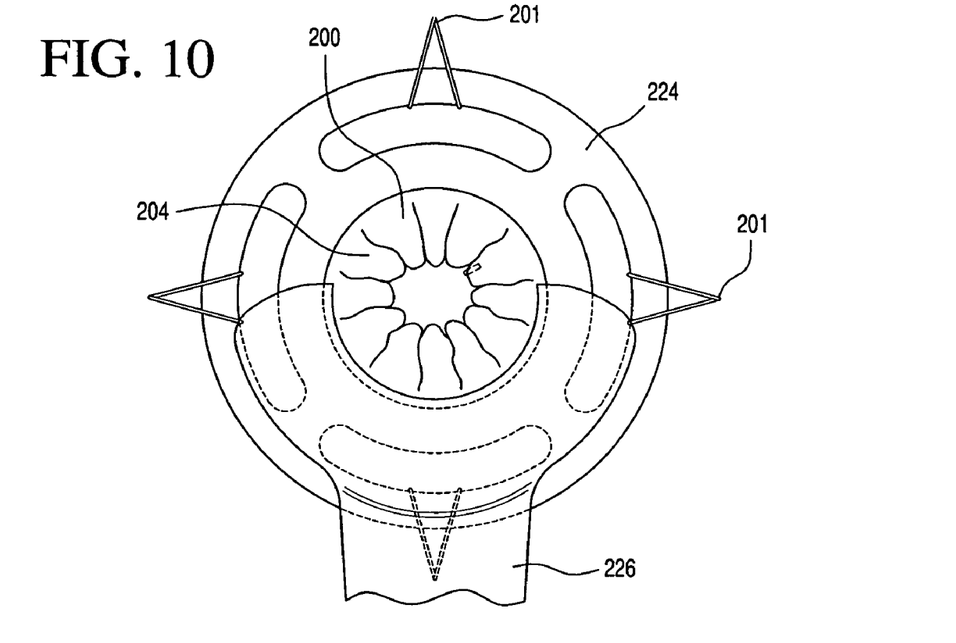
Figure 11:
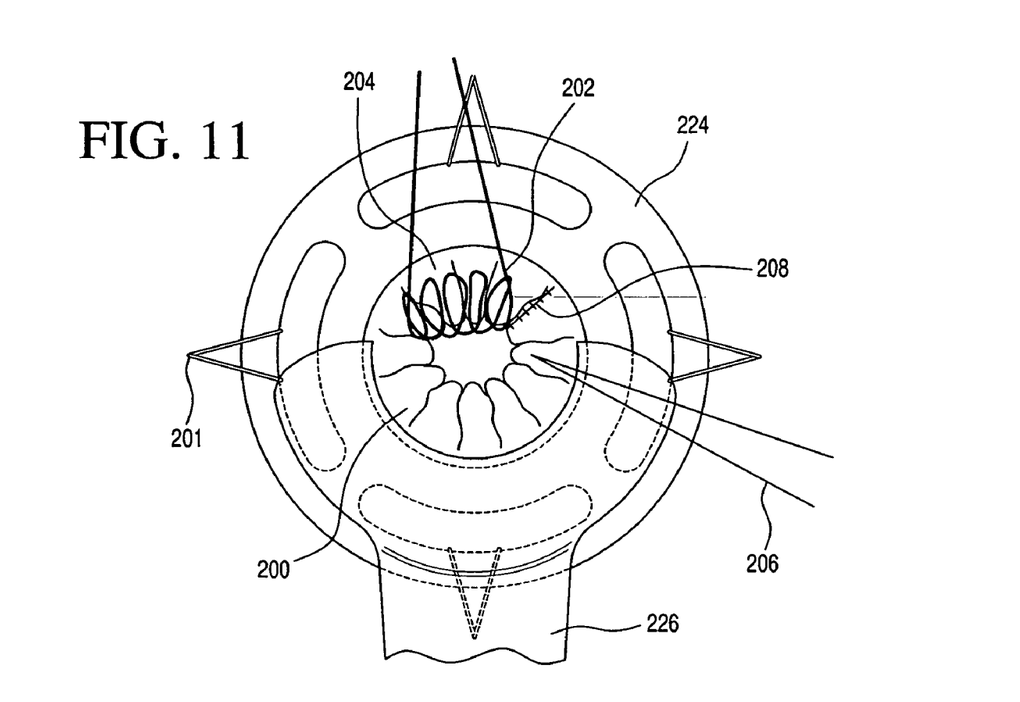
Figure 12:
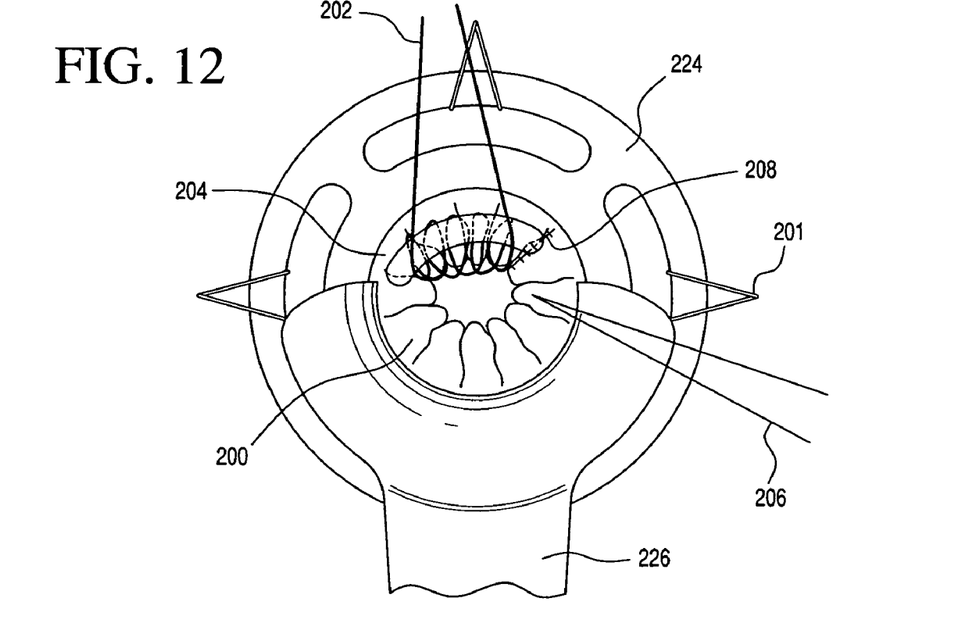
Figure 13:
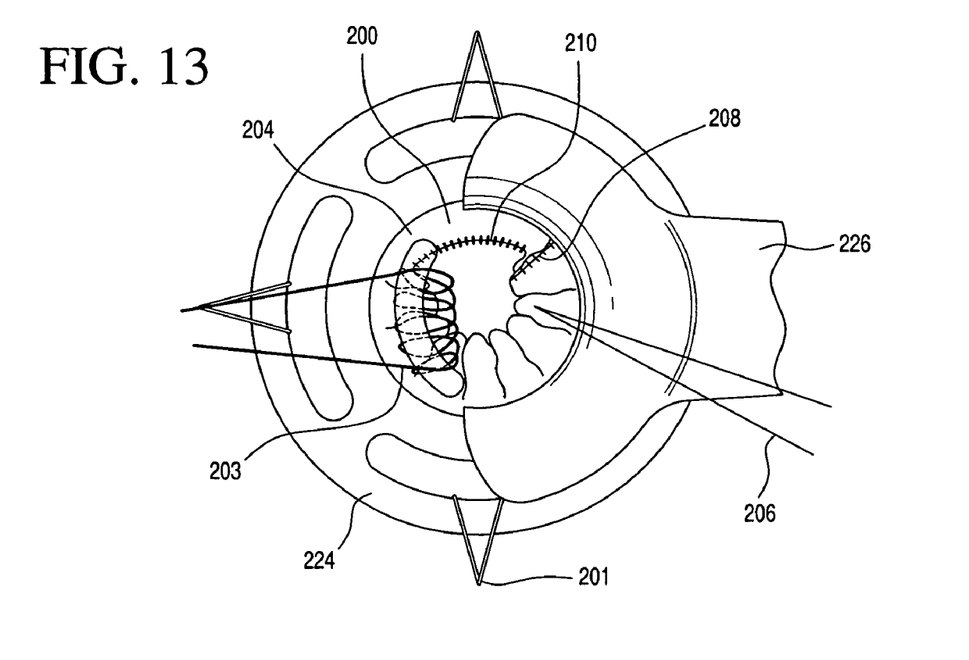
Figure 14:
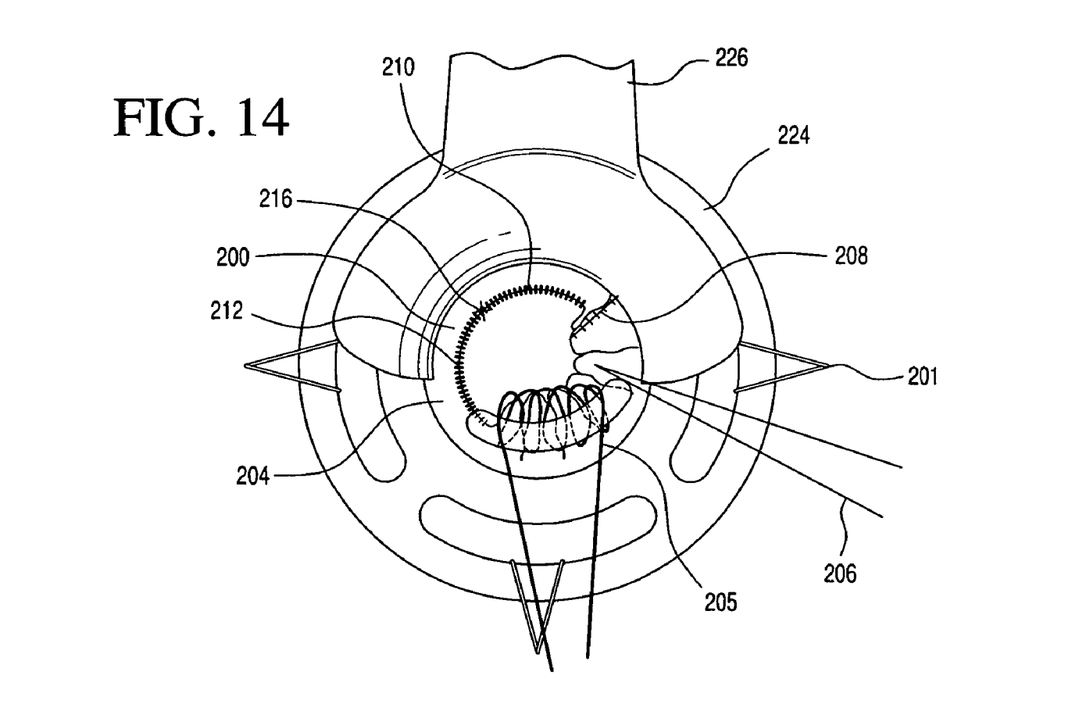
Figure 15:
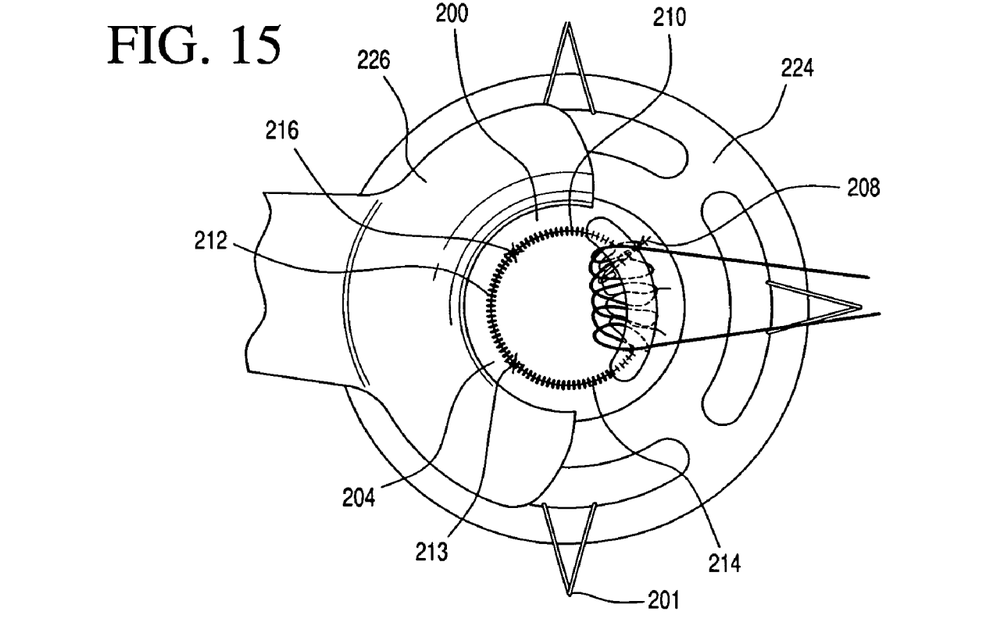
Figure 16:
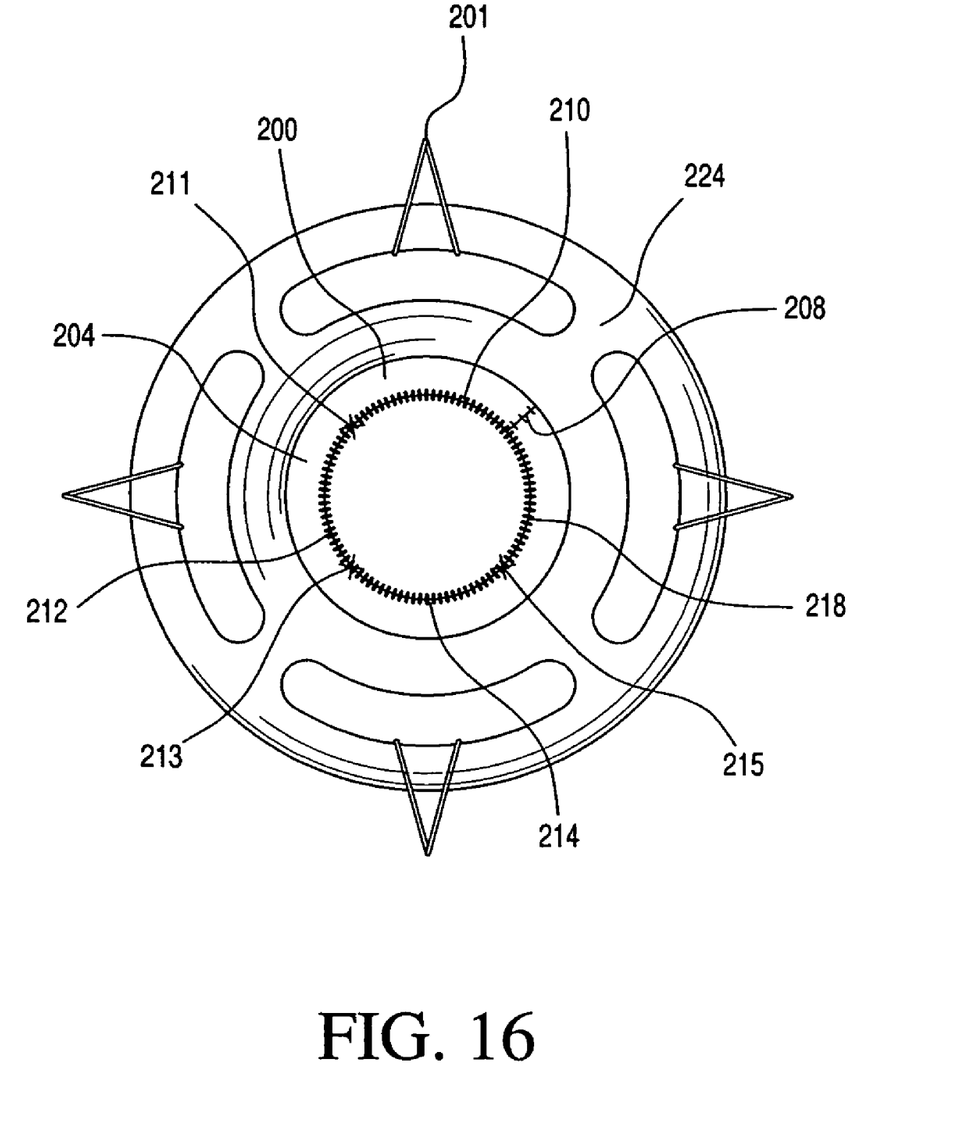

In practice, and referring to FIGS. 8 and 9, the curved cutter stapler 20 is used in conjunction with a dilator 224 and a spreader 226 in the performance of trans-anal resection in the following manner. Once the portion of the rectum 200 requiring resection is identified, the area is prepared in a conventional manner. In particular, and referring to FIG. 10, a dilator 224 is inserted and secured via a plurality of sutures 201 within the rectum. As mentioned above, the preferred envelope in which the end effector 80 must work has a diameter of approximately less than 40 mm. This is because a dilator 224 having a diameter of approximately 40 mm is preferably used in conjunction with the present procedure. Although a dilator having a diameter of approximately 40 mm is used in accordance with the present invention as this is believed to be the largest size dilator which can be used with most patients, those skilled in the art will appreciate that some patients will not accommodate a dilator of 40 mm and, therefore, dilators ranging in size from approximately 30 mm to approximately 40 mm are contemplated for use in accordance with the present invention. Similarly, a spreader 226 with a curvature slightly smaller than that of the dilator 224 may be used in conjunction with the present invention.

Thereafter, and with reference to FIGS. 11 to 16, a first whip stitch 202 is secured about the rectum 200 from a one o'clock position to an eleven o'clock position. The deep bites of the whip stitch 202 capture and fold the rectum wall 204 in a desired manner. In addition to the placement of a whip stitch 202 as discussed above, a traction suture 206 is positioned beneath the whip stitch 202 and is used to maintain tension on the tissue as the procedure is performed. Thereafter, a traditional linear surgical stapling instrument well known to those skilled in the art is positioned between the whip stitch 202 and the traction suture 206 to create a longitudinal staple line 208 in the rectal wall 204 at a position approximately at one o'clock. Thereafter, the present instrument 20 is placed in the rectal canal 200 and is positioned for capturing the rectal wall 204 held by the first whip stitch 202 positioned between one o'clock and ten o'clock. The instrument 20 is fired and a circumferential first staple line 210 extending from one o'clock to ten o'clock is created. Once this portion of the resection is completed, a second whip stitch 203 is placed from ten o'clock to seven o'clock to capture the rectal wall 204. The instrument 20 is then once again placed in the rectal canal 200 to capture the rectal wall 204 held by the second whip stitch 203 from ten o'clock to seven o'clock and the instrument 20 is fired creating a staple line 212 thereacross. In accordance with a preferred embodiment of the present invention, a figure eight suture 211 is then placed at the junction of the first and second staple lines 210, 212. Thereafter, a third whip stitch 205 is placed from seven o'clock to four o'clock and the instrument 20 is positioned and fired once again creating a third staple line 214 extending from seven o'clock to four o'clock. As with the prior step, a figure eight suture 213 is placed at the junction of the second and third staple lines 212, 214. Finally, the steps are repeated until the complete rectal section is fully stapled and resected adding a fourth staple line 218 and a figure eight suture 215.

While the preferred embodiments have been shown and described, it will be understood that there is no intent to limit the invention by such disclosure, but rather, is intended to cover all modifications and alternate constructions falling within the spirit and scope of the invention.

The invention claimed is:

1. A method for performing trans-anal resection, comprising:
    applying a first stitch about the rectum along a predetermined arc, wherein deep bites of the first stitch capture and fold a rectum wall;
    creating a longitudinal staple line in the rectal wall at a position adjacent the first stitch;
    positioning a curved surgical stapler instrument in the rectum for capturing the rectal wall held by the first stitch;
    firing the surgical stapler instrument creating a circumferential first staple line approximately along the arc defined by the first stitch;
    applying a second stitch about the rectum along a predetermined arc beginning at an end of the first staple line, wherein deep bites of the second stitch capture and fold a rectum wall;
    creating a longitudinal staple line in the rectal wall at a position adjacent the second stitch;
    positioning a curved surgical stapler instrument in the rectum for capturing the rectal wall held by the second stitch;
    firing the surgical stapler instrument creating a circumferential second staple line approximately along the arc defined by the second stitch;
    applying a junction suture at a junction of the first staple line and the second staple line; and
    repeating the steps of applying, positioning and firing about the circumference of the rectum until a predetermined portion of the rectum is fully resected.

2. The method according to claim 1, wherein the first stitch is a whip stitch.

3. The method according to claim 1, wherein the first stitch is applied from a one o'clock position to a ten o'clock position.

4. The method according to claim 1, wherein the first stitch is complemented by the application of a traction suture positioned beneath the first stitch to maintain tension on the tissue as the procedure is performed.

5. The method according to claim 4, wherein the longitudinal staple line is applied between the first stitch and the traction suture.

6. The method according to claim 1, wherein the junction suture is a figure eight suture.

7. The method according to claim 1, wherein the surgical stapler instrument includes a frame having a proximal end and a distal end, with a handle positioned at the proximal end and an end effector positioned at the distal end; the end effector being shaped and dimensioned for supporting a cartridge module; a firing mechanism is associated with the end effector and the cartridge module for selective actuation; and wherein the end effector has a radius of curvature optimized for trans-anal resection such that the end effector has a curvature of at most approximate a 40 mm diameter.

8. The method according to claim 7, wherein the end effector has a curvature of between approximately a 20 mm diameter and approximately a 40 mm diameter.

9. The method according to claim 7, wherein the end effector has curvature adapted to fit within an envelope having a diameter of approximately 40 mm.

10. The method according to claim 7, wherein the end effector has a curvature of approximately a 36 mm diameter.

* * * * *